United States Patent [19]

Hickam

[11] 4,121,288
[45] Oct. 17, 1978

[54] MAGNETIC TAPE TYPE SENSORS, METHOD AND APPARATUS USING SUCH MAGNETIC TAPE SENSORS

[75] Inventor: William M. Hickam, Churchill Borough, Pa.

[73] Assignee: Westinghouse Electric Corp., Pittsburgh, Pa.

[21] Appl. No.: 655,349

[22] Filed: Feb. 5, 1976

[51] Int. Cl.² .................... G06F 15/20; G01N 27/00
[52] U.S. Cl. .................. 364/497; 23/230 R; 324/213; 346/150; 360/6; 364/551; 422/62
[58] Field of Search ............... 324/34 TA; 73/27 A, 73/362 CP; 235/151.1; 360/6, 57, 59; 346/74.1, 150, 76 R; 340/173 CH; 23/230 R, 230 B, 252 R, 253 R, 253 TP, 259, 292

[56] References Cited

U.S. PATENT DOCUMENTS

| 3,714,564 | 1/1973 | Reinnagel ......................... 324/34 R |
| 3,868,059 | 2/1975 | Hickam et al. ..................... 236/15 E |

Primary Examiner—Joseph F. Ruggiero
Attorney, Agent, or Firm—C. M. Lorin

[57] ABSTRACT

A magnetic tape using as recording medium selected magnetic or non-magnetic material is used for on-line physical and chemical analysis by exposure to selected external agents, physical or chemical, causing permanent alterations in the material, and changes in the magnetic properties of the materials are sensed to read out the recorded information in correlation with the analyzed phenomenon or process for storage, monitoring or control purposes.

27 Claims, 10 Drawing Figures

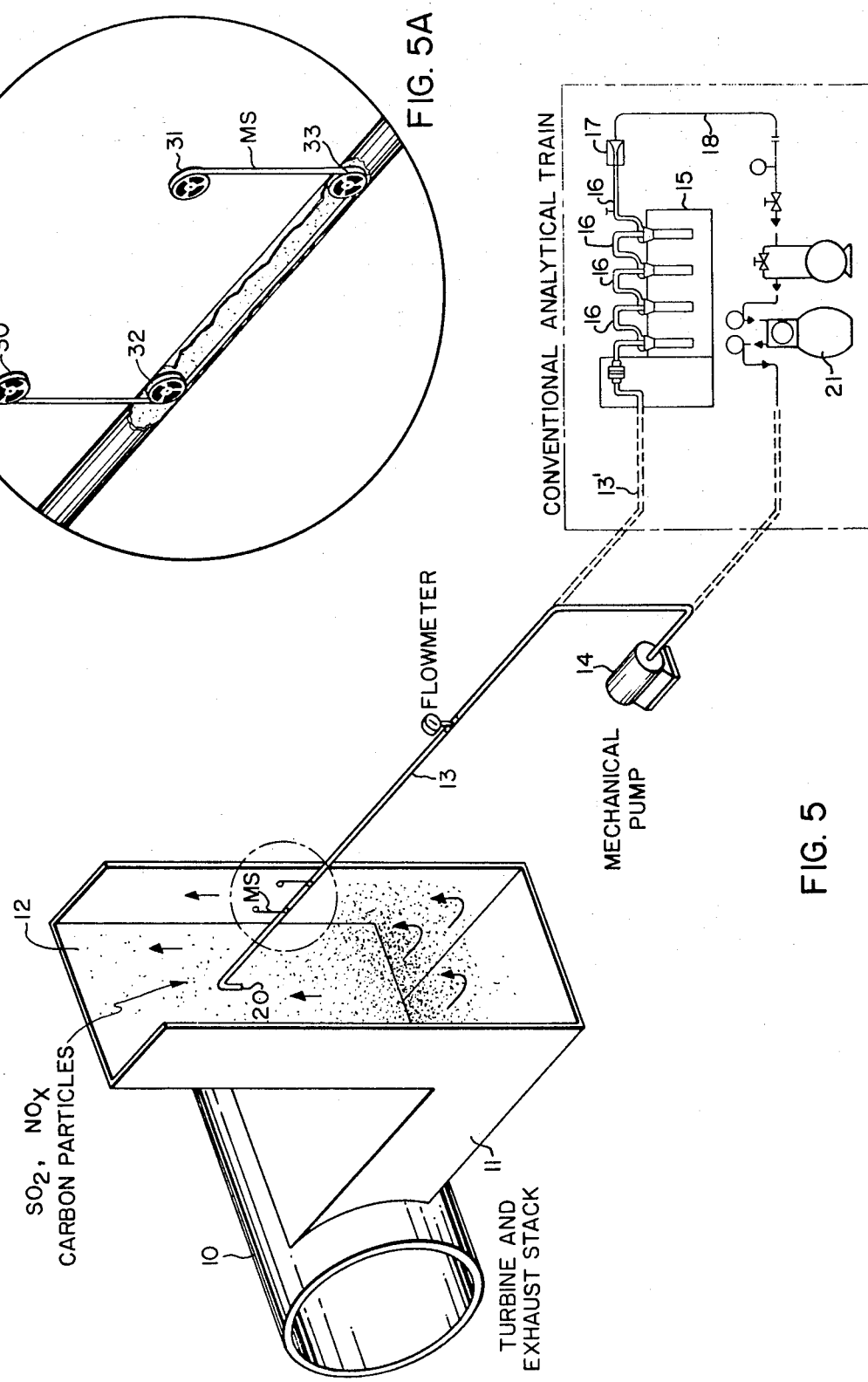

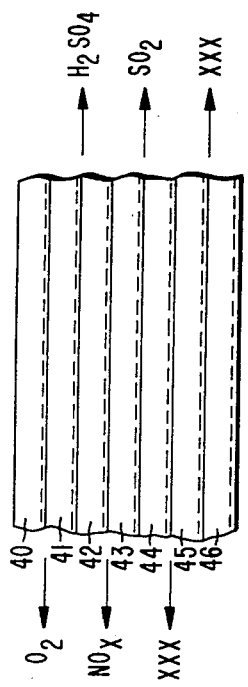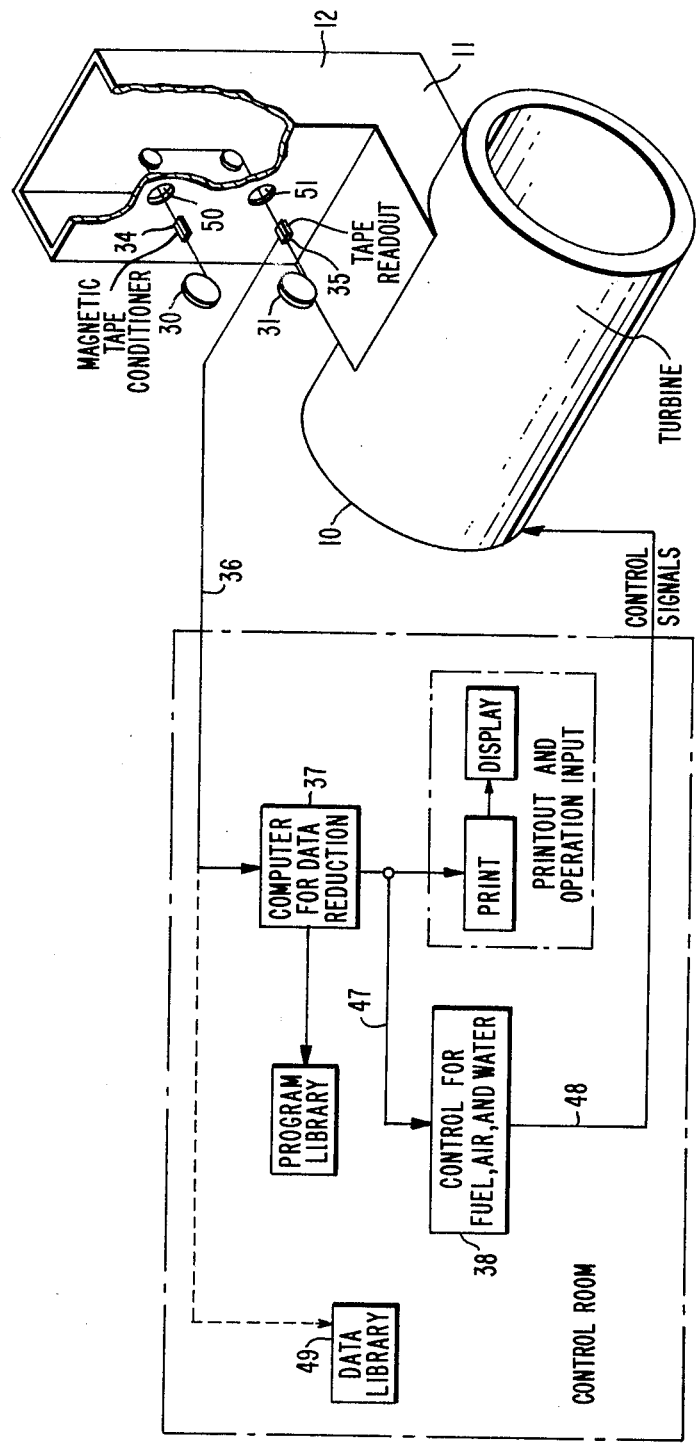

MAGNETIC TAPE TYPE SENSORS, METHOD AND APPARATUS USING SUCH MAGNETIC TAPE SENSORS

CROSS REFERENCE TO RELATED PENDING PATENT APPLICATIONS

The present application is related to the following concurrently filed patent application which is assigned to the same assignee as the present application: Ser. No. 655,350, which was filed on Feb. 5, 1976 by S. Spewock and D. C. Phillips.

BACKGROUND OF THE INVENTION

The invention relates to a novel and unique memory device for directly and continuously storing information relative to physical phenomena, to physical and chemical variables in an industrial process, and it also relates to a method of using such memory for data storage, for gas or liquid sampling, for sensing and recording process control variables, for monitoring and controlling an industrial process. The invention further relates to monitoring, sensing and control apparatus making use of such memory device and method.

The invention relates more particularly to memory devices including as storing element material possessing magnetic domains.

Memory devices are classified as non-destructive and as destructive. Non-destructive memory devices afford the possibility to write and read then erase and again write information data. The destructive type can permit repetitive reading, but the information is permanently stored in the storing medium. A read only memory is typical of this second type.

Magnetic memory devices generally take advantage of the fixed orientation taken by magnetic moments under the effect of an external magnetic field, thus creating a magnetic condition in the material which can be read at a later time. In that sense, a magnetic memory device, in the prior art, is always non-destructive since a change of orientation of magnetic moments does not affect the fundamental structure of the material.

Read-only memory devices, nevertheless, have been manufactured in the past with such non-destructive memories by combining memory elements and by so separating electrically the zones of exposure to external influence that changes effected in one zone become irreversible in relation to another zone.

A common type of magnetic memory device is the magnetic tape used in sound recording or as an integral part of a computer. The magnetic tape in sound recording is not exposed directly to the effects of the acoustic waves. A transducer device is necessary in order to convert the acoustic wave into an electrical signal used to impress on the tape a corresponding magnetic field altering the magnetic state of the tape. With the electronic computer, data information is stored into the tape at the input side by electromechanical means, which also are in substance a transducer.

Attempts have been made already in order to apply the magnetic storing quality of magnetic materials to the recording and monitoring of physical phenomena, and more particularly as a means for on-line chemical analysis of chemical reactions. For instance, in the U.S. Pat. No. 3,868,059 issued Feb. 25, 1975 to W. M. Hickam et al, assigned to the same assignee as the assignee of the present application, and entitled "Magnetic Bridge-Type Meter For Magnetically Permeable Particulate Matter", is described apparatus for the detection of fly ash emitted in the exhaust of a coal-fired furnace. The fly ash is admitted into the air gap of a permanent magnet associated with a magnetic bridge circuit and the change in inductance, thus caused, is detected as an indication of the operative conditions of the furnace. Therefore, the Hickam patent shows an apparatus having inherent magnetic characteristics which is directly exposed to an external physical phenomenon to be sensed and monitored, with the altered magnetic characteristics being used for detection and monitoring of the external physical phenomenon.

In the same vein, it is known from a paper presented at a Conference on Magnetic Materials held at Philadelphia in December 1975, entitled "Magnetic Gas Sensor" by Martin Rayl, Peter J. Woytowicz and Harold D. Hanson, to expose the core of an electromagnetic coil to oxidation-reduction reaction by gases, so that chemical changes occur in the material and the resulting change in inductance is measured as an indication of the presence of the gas.

Still, the prior art does not fulfill all the major needs of the industry regarding the acquisition of data relative to physical and chemical processes, or the determination of the chemical composition of gases, liquids, and solids. An absolute compositional analysis or merely the compositional variance from one acceptable reference standard may be required. The means for achieving compositional analysis are many and varied. They include the older wet chemical methods and numerous instrumental methods based on various scientific principles. In general, the analysis as currently practiced consists of five primary stages: (1) Sampling and sample conditioning, (2) Processing of sample through a selected analytical method, (3) Data readout and reduction, (4) Data storage, and (5) Compositional information feedback. Much has been said about these stages, their operative modes, their limitations, the possible applications, the problems of implementation, personnel requirements, and costs. For example, ASTM has published approved procedures for achieving compositional analysis of many materials. Various analytical instruments for laboratory use have been manufactured and extensively marketed to meet the needs for compositional analysis of materials. In many applications the laboratory instruments have been found inappropriate and insufficient, or too expensive in terms of initial cost and personnel cost. Their main drawback lies in the chemical uncertainties introduced by sampling, sample conditioning, and sample storage. Some instruments are capable of operating only on samples brought to ambient temperature and atmospheric pressure. Others require elaborate and variable data readout systems with personnel requirements for data reduction and storage. Most of these instruments do not lend themselves to automatic feedback control, a highly desirable feature for manufacture and manufacturing processes.

The present invention is a novel approach to acquiring and utilizing chemical and physical information on materials, industrial and chemical processing of materials, physical phenomena.

SUMMARY OF THE INVENTION

The present invention resides in a magnetic tape for on-line sensing of the physical and chemical properties of gases, liquids and solids, and in industrial applications of such magnetic tape to monitoring, sampling, recording, process control and data storage.

The magnetic tapes according to the present invention may be used for sampling, sensing, recording, controlling, and data storage of physical and chemical properties of gases, liquids, and solids. Magnetic and non-magnetic materials are placed on a flexible non-interfering substrate and passed, at a predetermined speed rate, through the physical or chemical environment to be analyzed and/or controlled.

Alteration in any or all magnetic properties of the materials, induced as a result of physical or chemical interaction, can be later read out by magnetic sensors. The noted changes in magnetic response are interpreted in terms of their relationship to definite chemical and physical properties of the environment to which they were exposed or variations thereof from specified or reference environment conditions. Processing of the magnetic information in terms of electric signals, may be performed by means of computers or other calculational and display media.

BRIEF DESCRIPTION OF THE DRAWINGS

FIG. 5 shows the use of the magnetic tape according to the invention to measure emission of gases in the exhaust stack of a gas turbine;

FIG. 5A is a magnified view of the magnetic tape according to the invention disposed within the exhaust stack of the system of FIG. 5;

FIG. 6 shows a magnetic tape according to the invention including a plurality of juxtaposed layers for multiple sensing applications;

FIG. 7 shows a magnetic tape according to the invention made an integral part of a process control system including feedback control, with the assist of a computer;

DESCRIPTION OF THE PREFERRED EMBODIMENTS

Figure 1:
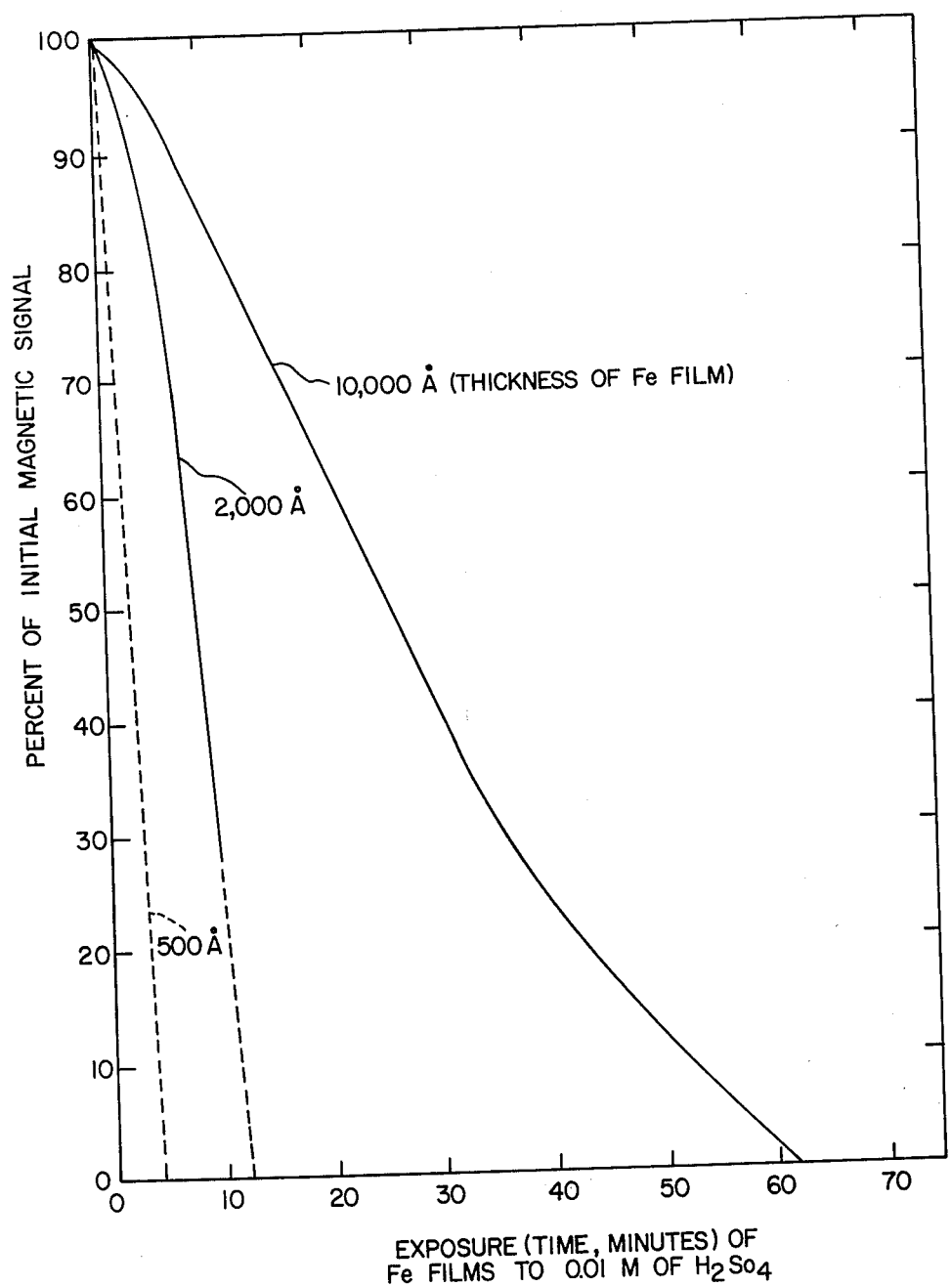
FIG. 1 is a curve showing graphically how exposure to sulfuric acid affects univocally the magnetic properties of a magnetic tape according to the invention.

The invention resides in a magnetic tape for online sensing of the physical and chemical properties of gases, liquids and solids, and in the industrial application of such magnetic tape to monitoring, sampling, recording, process control and data storage.

By "magnetic tape" in the description given hereafter is to be understood any magnetic or non-magnetic recording medium of sufficient length, of a given width or even as a wire, homogeneous or coated, made of magnetic or non-magnetic material in continuous form or discretely applied or deposited, which has been selected in accordance with the teachings of the present invention, as explained hereinafter. Common magnetic tapes, for instance, as used in sound recording techniques, are not excluded. In accordance with the present invention, contrary to common practice with this type of tape, it is contemplated to expose the tape directly to a physical or chemical phenomenon in order to alter the internal structure of the tape material. Such alteration is detected in the form of an electrical signal derived by a transducer sensing a magnetic field exhibited by the material as usual. To this effect, a signal having a well identified frequency characteristic is first stored into the tape. After alteration of the tape by selective exposure to the environment, noticeable changes in the frequency pattern of the detected signals are obtained at different locations along the tape which provide information in real time as the tape is unwound.

As an illustration of this sensing method, a magnetic tape of the common type in sound recording, specially conditioned by prerecording of an audio signal, has been exposed to sulfuric acid in solution at a concentration of 6 moles. Wherever the tape has been so exposed, and to a corresponding degree, the detected audio signal exhibits a marked change in the audio frequency as originally stored.

More generally, sulfuric acid emissions in the atmosphere result from fossil fuel burning in stationary and mobile systems. The molarity of sulfuric acid aerosol emitted into the atmosphere is humidity dependent. At ambient temperatures, the weight concentration of $H_2SO_4$ in the aerosol changes from 9 to 64 weight percent as the relative humidity changes from 99% to 10%. Sulfuric acid can also be detected at various levels in the exhaust from fossil fuel fired installations. The novel and unique concept which is the gist of this invention lies in the observation made that magnetic tapes when exposed to sulfuric acid in situ constitute sensitive detectors of the acid. The method of detection of the presence of sulfuric acid with magnetic tape is particularly attractive since it makes it possible with a continuously running tape to monitor as a function of time the changes in acid concentration. No complex apparatus is needed at any monitoring station. Also, more generally, instead of using conventional magnetic tape, the detecting method according to the invention may also advantageously make use of carefully selected materials formed into a tape, preferably as an outside layer mounted on a substrate. The layer may be glued, sintered, deposited, or otherwise fixed onto or into the substrate.

A test of operability of the method according to the present invention has been conducted with copper rods of $\frac{3}{8}$ inch diameter electroplated with iron. The coating covered the end of the copper rod and extended approximately 2 inches along the length. The coated area was 15.9 cm$^2$. The quantity of iron deposited was determined electrochemically. Coating thicknesses of 500 Å, 2000 Å, and 10,000 Å were obtained, assuming a coating density of 7.86 g/cm$^3$. The total weights of iron in the coatings were 0.6, 2.5, and 12.5 mg.

The iron films were exposed to 0.01 molar sulfuric acid solution for varying times. The changes in ferromagnetic properties of the coating, as a result of reaction with $H_2SO_4$, were measured with a magnetic bridge of the type shown in the above-mentioned Hickam patent. Such magnetic bridge incorporates Hall effect sensors to sense induced magnetic changes. It can detect as little as 200 Å of reacted ferromagnetic material on a surface of a few square centimeters.

Sulfuric acid reacts with a number of metals to form the corresponding sulfate. In the case of iron, the ferromagnetic metal is converted first to ferrous sulfate, which can react further with the oxygen of the air to form ferric sulfate. Both sulfates are only paramagnetic and show negligible interaction with a magnetic field compared to the interaction of the corresponding amount of iron metal which has reacted. Monitoring the changing interaction with a magnetic field of an iron metal film exposed to exhaust gases can, therefore, constitute a very sensitive means for determining the quantity of entrained sulfuric acid particles.

The results given in FIG. 1 illustrate the use of this sulfuric acid monitoring concept. Electrochemically deposited iron films of known initial thickness were exposed for varying lengths of time to a 0.01 molar sulfuric acid-water solution. Exposure resulted in conversion of a portion of the iron to ferrous and ferric sulfates and a corresponding reduction in the ferromagnetic interaction of the specimen with a magnetic field. The reaction time, at room temperature, required for complete reaction of the 2000 Å iron film was approximately 12 minutes as compared to 60 minutes for complete reaction of the 10,000 Å film. The initial weight of iron in the 2000 Å film was 2.5 mg.

A 100 Å thick ferromagnetic film covering 5 cm² can be detected with the magnetic bridge. In the case of iron, the film would weigh 0.04 mg. The detection limit for S in the form of $H_2SO_4$ is of the same order of magnitude.

In a more general context, where chemical reaction is involved, the most desired materials that can be used for sensing the chemical and physical properties of the environment are iron, nickel, cobalt and compounds and alloys of these elements. Chemical reaction products leading to changes in magnetic properties may include the formation or reduction of oxides, carbides, nitrides, hydrides, chlorides, and sulfides of iron, nickel, cobalt and other elements which undergo changes in magnetic properties as a result of chemical reaction or physical change. More generally, reactions such as oxidation, reduction, carburization, halogenization, sulfonation, are among the contemplated forms of reactions.

Besides chemical agents, various physical agents in the environment can alter the material in such a way that magnetic properties will be produced (if the material is initially non-magnetic) or increased, or diminished (if material is initially magnetic).

The structural changes in the material under specific chemical and physical agents are listed in Tables 1 and 2, herebelow, respectively.

TABLE 1

Chemical Agents Which Increase or Decrease the Magnetic Properties of Certain Materials

| | Initial Reactant | Chemical Agent | Final Product | |
|---|---|---|---|---|
| Magnetic Materials | Ni | $H_2SO_4$ | $NiSO_4$ | Non-Magnetic Materials |
| | Ni | $SO_3$ | $NiSO_4$ | |
| | Ni | $O_2$ | $NiO$ | |
| | Ni | $HNO_3$ | $Ni(NO_3)_2$ | |
| | Fe | $CO_2$ | $FeO$ | |
| | Fe | $HCl$ | $FeCl_3$ | |
| | Fe | $HF$ | $FeF_3$ | |
| | Fe | $HNO_3$ | $Fe_2O_3$ | |
| | Fe | $O_2+H_2O$ | $FeO$ | |
| | Fe | $H_2O$ | $FeO$ | |
| | Fe | $O_2$ | $Fe_2O_3$ | |
| | Fe | $NO_2+H_2$ | $FeO$ | |
| Non-Magnetic Materials | Cr | As | CrAs | Magnetic Materials |
| | $Cr(OH)_3$ | $O_2$ | $CrO_2$ | |
| | $Fe_2O_3$ | $H_2$ | Fe | |
| | $Fe_2O_3$ | $SO_2$ | $Fe_3O_4$ | |

TABLE 2

Physical Agents Which Increase or Decrease the Magnetic Properties of Certain Materials

| | Initial Reactant | Physical Agent | Final Product | |
|---|---|---|---|---|
| Non-Magnetic Materials | $Cr(NO_3)_3$ | Heat | $CrO_2$ | Magnetic Materials |
| | 304 Stainless Steel | Cold working | 304 stainless steel (magnetic) | |
| Magnetic Materials | Ni | Heat to Curie point (360° C) | Ni | Non-Magnetic Materials |
| | Fe | Heat to Curie point (768° C) | Fe | |
| | Co | Heat to Curie point (1120° C) | Co | |
| | Ni | Any physical agent that diminishes the amount of material present; e.g., abrasion, solvent dissolution, etc. | Ni | |
| | Fe | | Fe | |
| | Co | | Co | |

If a correlation can be established between the physical, or chemical, agent altering a material and the magnetic change produced by the alteration, the agent can be monitored. In this way a change in the magnetic properties will yield information regarding the nature and magnitude of the particular agent involved.

The induced magnetic changes in a tape may be continuous or discrete along the tape. Physical alteration may encompass the entire volume of the tape, or only its coating. The exposed layer may be in the form of a thin film, exhibiting magnetic changes as a function of the depth of the coating in response to time of exposure and/or change in the concentration of selective reactants. The sensing coating itself may be discontinuous. It may consist of a single, or of several juxtaposed materials. The nature of the coating may be such that it collects magnetic particles from the environment, for example, fly ash, when exposed to the exhaust of a gas turbine.

Such magnetic tapes are used in accordance with the present invention for sampling, sensing, recording, and controlling environments, as a result of alterations through chemical or physical action involving the magnetic properties of the tapes. Physical agents contemplated for such alterations of the tape include temperature, high energy ion sputtering, neutron bombardment resulting in swelling, and defect centers caused by electron and gamma ray bombardment.

The magnetic tapes to be used for sensing physical and chemical properties may have several forms. Included among the possible configurations of the disclosed tapes are solid wires, solid ribbons, continuous and discontinuous coated wires and/or ribbons, single or multiple track coated ribbons, and discs. The preference will depend on the particular application and its requirements.

The ways a tape can be altered when sensing the physical and chemical properties of the environment to be analyzed are varied and are many. Specific examples include: (1) demagnetization as would occur for magnetized iron on exposure to $H_2S$ under conditions to form iron sulfide; (2) development of a magnetic film as does occur with exposure of Inconel to steam and stainless steel to high temperature liquid sodium; (3) demagnetization by sputtering of a magnetic iron or magnetic oxide coating exposed to high energy ion bombardment; (4) change in magnetic properties as a result of crystal growth by annealing as reported for CUBEX; and (5) demagnetization as a result of swelling under exposure to a high neutron flux.

In general, it is preferred that the specially designed magnetic tapes pass directly through the environment for which the monitoring of physical and chemical properties are sought. However, in some instances it may be desirable to use established sampling procedures and place the transported tape sensors within the sampling system instead of directly through the environment.

Figure 2:
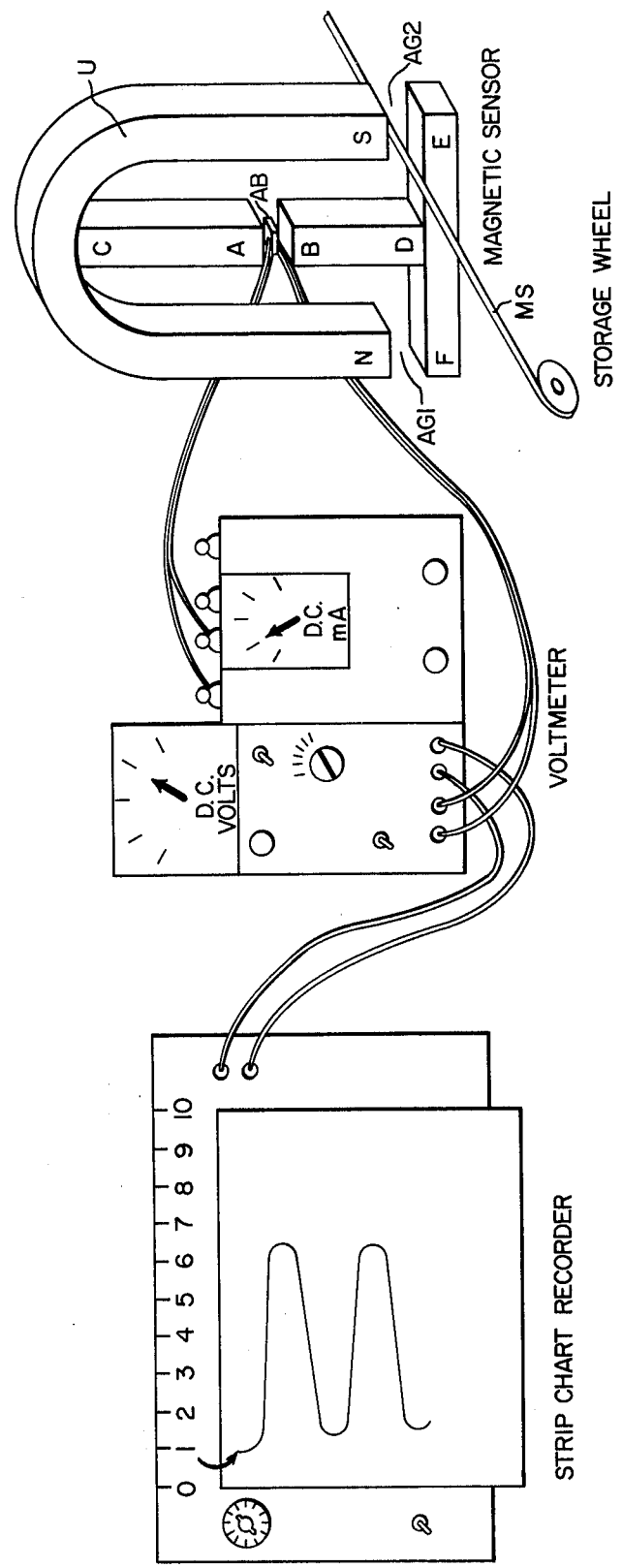
FIG. 2 illustrates apparatus according to the present invention for deriving by magnetic sensing a measurement of industrial process physical or chemical parameters stored as data in a magnetic tape according to the present invention.

Once the changes have been induced in the magnetic structure of the tape material, they can be read by a conventional inductance or magnetic field measuring instrument. As a result, chemical and physical measurements are in fact made by magnetic means. However, as illustrated in FIG. 2, a special equipment has been conceived to perform these measurements. Perturbations in the field generated by a permanent magnet U are sensed by a Hall effect element at AB.

The magnetic sensor comprises a horseshoe-shaped magnet U separated by two equal air gaps $AG_1$, $AG_2$ from a soft iron bar (FE). Two additional soft iron bars (CA and BD) connect the top center of the horseshoe magnet U with the center of the soft iron bar FE. Cemented between CA and BD is a small Hall effect element AB. The Hall element has two leads which carry a constant direct current input, and two leads which carry a continuous electrical output signal. The magnitude of the electrical output (or Hall voltage) is determined by the strength of the net magnetic field which the Hall element senses, as well as the size of the direct current input. When the current is constant, the net magnetic field is determined by 1) the strength of the magnet, 2) the nature of the magnetic material, and 3) the amount of magnetic material. The resulting electrical signal can be read from a voltmeter, or it can be fed to a recorder. Perturbations are caused by the presence of the tape magnetic material MS in proximity to the sensor portion of the apparatus, e.g., in one of the air gaps $AG_1$, or $AG_2$. The magnitude of the signal produced depends upon the nature and amount of magnetic material. The instrument of FIG. 2 is designed to operate over a wide range of sensitivities, and capable of detecting very small perturbations. Small changes in the magnetic properties of a material can therefore be detected.

Table 3 herebelow lists the characteristics of some ferromagnetic materials. For a given magnet strength, the higher the material permeability, the larger will be the the net magnetic field sensed by the Hall element, everything else remaining constant. Also, the greater the amount of magnetic material, the larger the field sensed.

TABLE 3

| | Some Properties of High-Permeability Materials | | | | | |
|---|---|---|---|---|---|---|
| Name (Composition) | m.p. (° C) | Curie Pt. (° C) | Max. Permeability | Coercive Force (oersteds) | Saturation Induction (gausses) | Saturation Hysteresis (ergs/cm³) |
| Iron (.2 impurity) | 1537 | 768 | 5000 | 1.0 | 21,500 | 5000 |
| Cobalt (99 Co) | 1495 | 1120 | 250 | 10 | 17,900 | 2000 |
| Nickel (99 Ni) | 1455 | 360 | 600 | 0.7 | 6,100 | 2000 |

If the device is symmetrical and the material present in the air gaps is the same, no magnetic field will be detected by the Hall element and no Hall voltage will be registered. Both the north and the south poles of the magnet "attempt" to induce a pole of opposite polarity in the soft iron bar at A. If the geometry is perfect, the two induced poles exactly cancel. Under the same symmetrical conditions, the poles induced at B cancel as well.

If a magnetic material is introduced into one of the two gaps, but not into the other, the effective permeability of the gaps is changed and the two induced poles at B no longer exactly cancel. The resulting net field produces an electrical signal — the Hall voltage — as described above. This signal can be read from a meter or it can be fed to a recorder. In addition, both the Hall voltage signal and the recorder output can be amplified so as to accommodate a wide range of materials and conditions.

Figure 3:
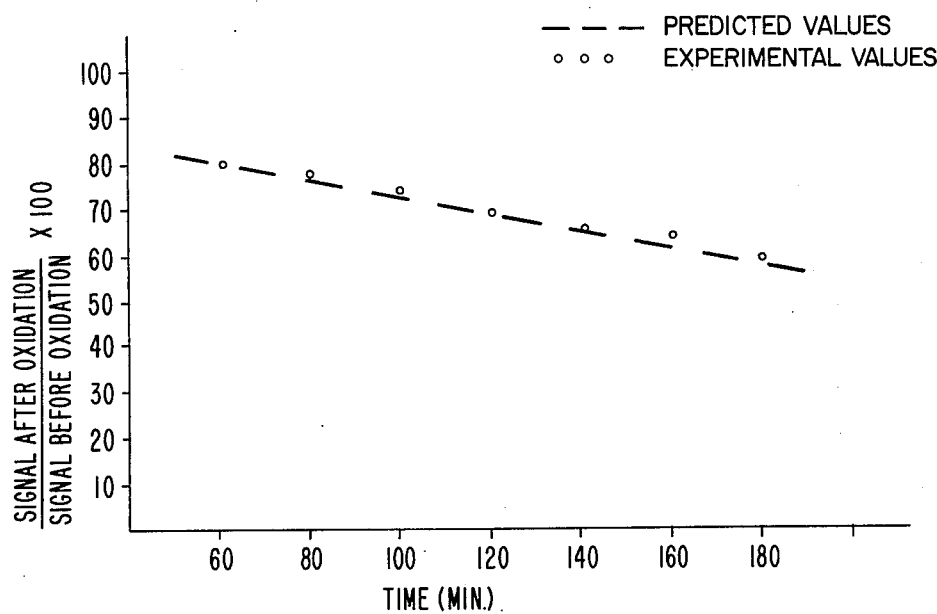
FIG. 3 shows as a function of time how oxidation in a nickel foil affects the signal detected with the apparatus of FIG. 2.
Figure 4:
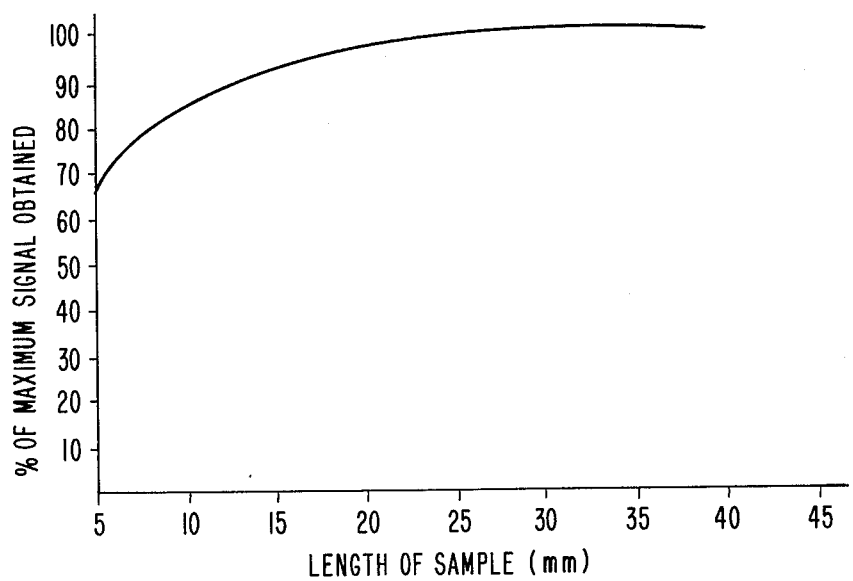
FIG. 4 shows the variation of the signal detected in the case of FIG. 3 as a function of the distance from the center of the air gap in which the tape is being placed.

The apparatus can be made more sensitive, in order to amplify the electrical signal, by (1) increasing the magnet's strength, (2) decreasing the size of the air gap, (3) increasing the current. The electrical signal or Hall voltage is proportional to the size of the current and to the strength of the magnetic field it senses. The magnitude of the field sensed is determined by the strength of the magnet as well as by the size of the air gaps. Since the air gap represents a "resistance" to the magnetic flux, a smaller air gap results in the Hall element sensing a larger magnetic field. The range and sensitivity of the apparatus illustrated in FIG. 3 was determined using 1 mil (0.0025 cm) pure nickel foil. The electrical signal produced by the foil varies with the length, width, and thickness of the sample. The signal is directly proportional to sample thickness. Variation in the signal with sample length is shown in FIG. 4. FIG. 4 also shows the dimensional range of the sensed information, namely of about 21 mm. Thus, magnetic flux passed through materials is sensed up to 10.5 mm to either side of the center of the magnetic pole involved. If the material is further away than 10.5 mm, no signal is received since as shown the curve becomes flat beyond that distance. For the 1 mil (0.0025 cm) nickel foil examined, accuracy of measurement within 2 percent can be obtained. The minimum variation in nickel foil thickness detectable by the apparatus of this geometry is, therefore, approximately 2900 Å.

In order to monitor magnetically a chemical or physical agent, the following criteria must be met. (1) The agent must alter the magnetic property of the magnetic or non-magnetic material in a unique, uniform, and reproducible manner. (2) The magnitude of the electrical signal must be related to the amount of material in the sample which has been altered in its magnetic properties. If length and width of a magnetic sample are kept constant, the signal must be related to sample thickness.

The apparatus of FIG. 2 can be used for the detection of oxygen with a tape of nickel as the active metal. Nickel metal, which is magnetic, reacts with oxygen to form nickel oxide, which is non-magnetic. The actual thickness of the oxide layer formed on the metal surface is determined by the partial pressure of oxygen, as well as by the duration and temperature of oxidation. The longer the time, the more elevated the temperature, the higher the oxygen partial pressure, the greater is the oxide thickness. When time and temperature are held constant, there is a one to one relationship between the oxide thickness and the oxygen partial pressure. If oxidations are carried out using nickel foil of a given thickness (say 1 mil, e.g., 0.0025 cm), for a given partial pressure there will correspond not only a characteristic oxide thickness, but also a characteristic thickness of the nickel foil remaining unoxidized. During measurement, the unoxidized portion of the sample causes an electrical signal; as the extent of oxidation increases, the thickness of nickel remaining unoxidized decreases, and so does the electrical signal. Conversely, the larger the oxygen partial pressure, the smaller the electrical signal.

The preceding satisfies the above-mentioned first criterion to be met regarding the effect of various oxygen partial pressures on nickel when time and temperature remain constant. If the above-mentioned second criterion can also be met, it will be possible to monitor a partial pressure of oxygen as a function of nickel oxidation. That this can be done is demonstrated by the following procedure.

Nickel oxidation data are gathered which relate oxide thickness to time when temperature and oxygen partial pressure remain constant. These data permit predictions about the relative magnitudes of electrical signals obtained from oxidized nickel samples. If the second criterion is met, the following relationship should hold: When a strip of nickel foil produces a given electrical signal prior to oxidation, after oxidation it produces a smaller signal. The ratio of these signals should be identical to the ratio of the thickness of the unoxidized sample to the thickness of the nickel foil remaining after oxidation.

This relationship was verified experimentally. One mil (0.0025 cm) strips of pure nickel foil were exposed to 0.1 atm of oxygen at 1000° C. for varying periods of time. After each sample cooled, it was passed through the magnetic sensing apparatus, which recorded an electrical signal. It was found that the magnitude of every signal was within 2 percent of that predicted on the basis of the thickness of the oxide layer formed, as described above. These results are evidenced by FIG. 3 and the following Table 4:

TABLE 4

Predicted vs. Experimental Values for the Oxidation of Nickel in 0.1 atm of $O_2$ $$\frac{\text{Electrical signal produced by oxidized sample}}{\text{Electrical signal produced by unoxidized standard}} \times 100$$

| Time (min) | Values predicted on basis of Gulbransen-Andrew data | Experimental Values | % Difference |
|---|---|---|---|
| 60 | 80.2 | 80.2 | 0 |
| 80 | 76.5 | 77.3 | 0.8 |
| 100 | 73.0 | 75.0 | 2.0 |
| 120 | 69.7 | 71.4 | 1.7 |
| 140 | 66.3 | 67.0 | 0.7 |
| 160 | 63.1 | 65.9 | 2.8 |
| 180 | 59.1 | 56.8 | 2.3 |

The conclusion is that both criteria (1) and (2) are met. Therefore, it has been proved that nickel oxidation can be used to monitor the partial pressure of oxygen. More generally, it can be concluded that any chemical or physical agent which fulfills such criteria can monitored.

From the above it further appears that the proposed magnetic measuring concept is widely applicable. Modifications of the magnetic apparatus permit its operation over a large range of sensitivities. In addition, numerous magnetic and non-magnetic materials exist that can be altered as described earlier. This makes it possible to measure various chemical and physical parameters in an industrial process provided such chemical and physical agents are capable of altering magnetic and non-magnetic materials so as to cause a reduction in the amount of magnetic material in the former instance, or to create a magnetic compound in the material of the second instance. Table 1 lists a number of such alterations. Thus, the nature and importance of any such agent, since it produces an alteration which is translated into modified magnetic properties, can be detected by a measurement of magnetic property.

The method according to the invention makes it possible to monitor systems having as process variable such diverse chemical agents as oxygen, hydrogen, sulfur, phosphorus, and the halides. When choosing a material appropriate for monitoring a particular chemical or physical parameter, consideration should be given to both the system in which the measurement is to be made and the materials to be used. A given material may be altered by a number of different agents, other than the one which is to be measured. Side reactions may interfere with, or prevent, the desired reaction, or they may produce magnetic changes of their own. Extraneous agents which could cause such side reactions must be identified. The measurement derived in accordance with the present invention may be related to one or more of the chemical or physical parameters of interest. The man skilled in the art will be able to interpret the results in terms of the physical, or chemical agent, which is relevant to the measurement.

Referring to FIGS. 5 and 5A, a magnetic tape sensor according to the invention is shown applied as a sampler in situ of the conditions in the exhaust stack of a gas turbine. The installation includes a turbine 10 having an exhaust conduit 11 and a stack 12 exhausting gases including $So_2$, $No_x$ and carbon particles. Sampling is effected with a nozzle 20 mounted at the extremity of a pipe 13 in which the fluid is sucked by pumping action of a mechanical pump 14. Conventionally, the sampled fluid is carried from the pipe 13, via 13′, through a chemical analyzer including concentrating devices 16 immersed in a solution bath 15. The samples are passed via pipe 18 to a flowmeter 22 and an analyzer proper 21. Instead of the analytical train of the prior art, the present invention calls for placing in the pipe 13 a magnetic sensor MS in the form of a continuous tape set in motion from a pay-off reel 30 to a loading reel 31, between two ports 32, 33 provided in the pipe wall (see FIG. 5A).

Referring to FIG. 6, the tape is preferably comprised of several layers 40-46 juxtaposed across the width of the tape. Each layer consists of material so selected as to be capable of being altered in its physical and chemical structure by one specific physical agent characteristic of the fluid sample in pipe 13. Some of the layers are shown for the purpose of illustration as related to sensing $O_2$, $H_2SO_4$, $NO_x$. Other agents may be the magnetized particles of fly ash. Temperature is also an important parameter in the stack of a turbine. As a matter of fact, the magnetic sensor according to the present invention is particularly suitable for sampling and testing in a zone at high temperature, because a ribbon or wire of tape can easily be manufactured to withstand temperatures from ambient to 1600° C., the temperatures more generally encountered in practice being in the range of 500° C. to 900° C.

Referring now to FIG. 7, the magnetic sensor according to the present invention is shown as an integral part of a process control system. The magnetic sensor is here directly placed in the stack 12 of the turbine exhaust. The tape coming from the pay-off reel 30 enters the stack from one port 50 and exits through a second port 51 toward the loading reel 31.

From the preceding explanations, it is clear that the initial state of the tape MS may be a state of magnetization, as well as one of neutral magnetic condition. In the first instance, the state of magnetization may be enhanced, or reduced, as a result of physical destruction or alteration of the medium. In the second instance, physical alteration of the medium causes a state of magnetization to build up in the material. More generally, by "magnetic tape" in the present description, should be understood a tape — in the form of a ribbon or wire — homogeneous, or heterogeneous, integral or coated — including at least in part or with a predetermined repetitive pattern along its length, material which is paramagnetic, ferromagnetic, but also which may be antiferromagnetic or ferrimagnetic. To be capable of sensing the presence of an agent altering the chemical or physical nature of the material by sensing a correlative alteration by magnetic field detecting devices, it is required that, following exposure, a change in the magnetic state of the material will take place which change can be detected. In other words, the tape MS may be in its original state or it may have been conditioned right before exposure. Illustratively, FIG. 7 shows the tape being passed through a magnetic tape conditioner 34 before entering port 50. A tape read-out device 35 takes up the tape after the exit port 51 any records the information gathered while passing through the stack.

FIG. 7 also illustrates how the magnetic tape MS can be integrated in a process control system. Data derived from the tape read-out device 35 is supplied via line 36, to a computer 37, where it is treated electronically.

Since data information on line 36 is continuously supplied as a function of time while tape MS is unrolling into the stack 12 of the turbine, adaptive process control technique is easily applied to the system. The computer performs calculations using all the bits of information provided by the tapes in the stack. Temperature and gas composition, dust particles, are known thereby to provide all the elements for an on-line analysis of the quality of turbine operation in real time. From such calculations, control parameters are established by the computer, for instance, the feed requirements of fuel, air, $H_2O$. These requirements are translated as input data to a control unit 38 via line 47, and the control unit applies control signals, via line 48, to the organs of the turbine 10.

The tapes MS, properly indexed with respect to time and operative turbine unit, remain available as a file history and can be stored in a data library 49.

The magnetic tape according to the present invention lends itself also to sensing with feedback control.

Although illustrated only for a turbine, both mobile and stationary combustion systems, the invention is applicable to furnaces and combustion chambers which would include indeed engines of automobiles and planes, for instance.

Figure 8:
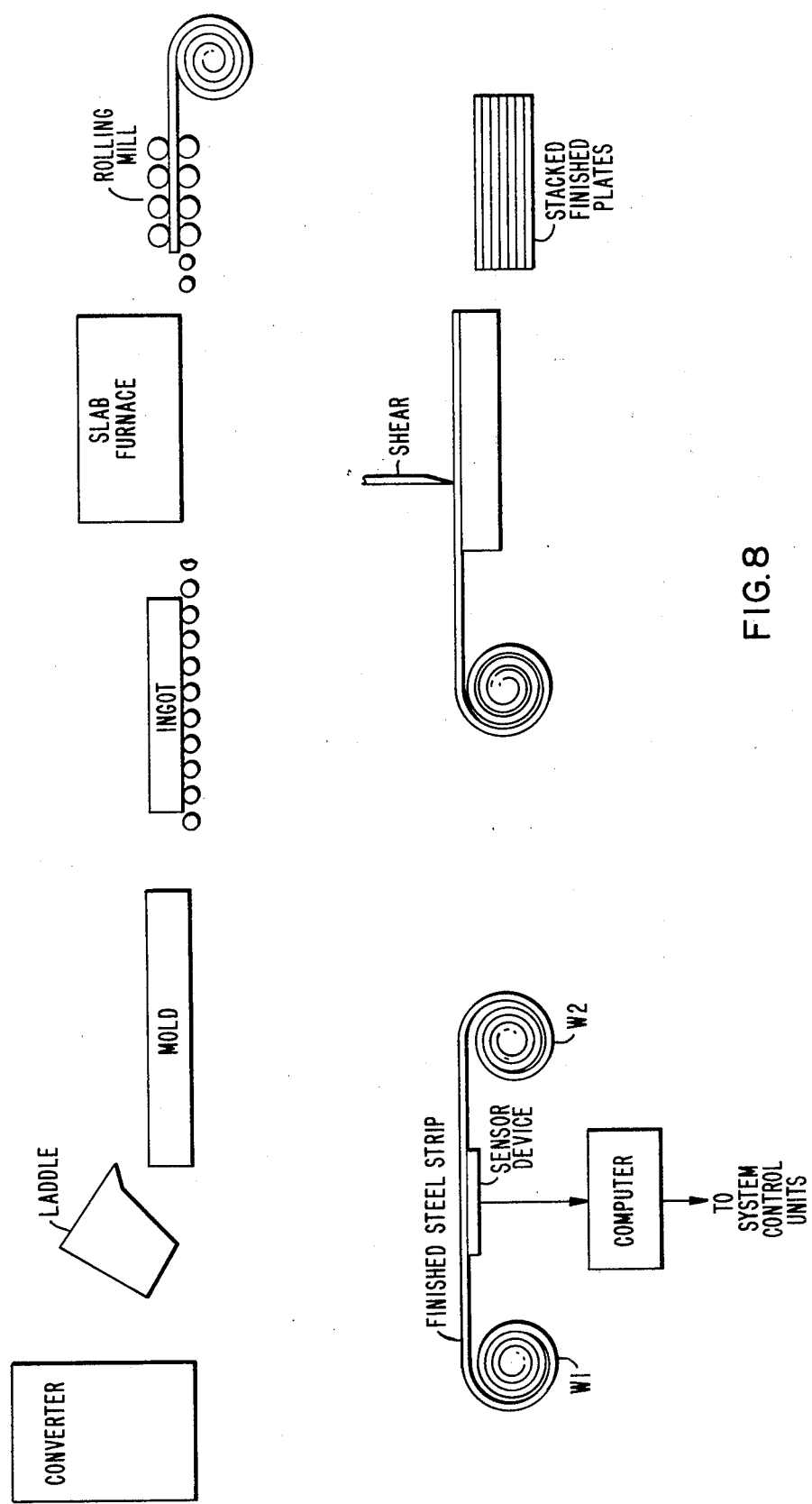
FIG. 8 shows steel processing in a steel mill controlled in accordance with the present invention by directly sensing, in accordance with the invention, the magnetic properties of steel strips before shearing into transformer plates.

A novel and unique mode of manufacturing magnetic plates of the desired quality for the transformer industry is illustrated in FIG. 8. The process line for the manufacture of magnetic plates is schematized by its major steps from the converter furnace to the shear cutting the metal strip after rolling to the desired thickness. The present invention for this particular application provides on the process line an additional step consisting of sensing the magnetic properties of the final product while still in the form of a strip. This can be done on the rolling mill itself, or at a different location, as shown in FIG. 8. Between a pay-off reel $W_1$ and a loading reel $W_2$, the coil of strip material is uncoiled and sensed by a magnetic sensor. The information derived is conveyed to a computer which, by computational analysis, determines which one of the control units should be acted upon in the overall steel manufacturing process in order to obtain on the pay-off reel $W_1$ a metal having the desired magnetic properties. Once the manufacturing conditions have been found acceptable, the loading reel $W_2$ is unloaded at the shearing station thus insuring the production of transformer plates having the required characteristics.

In this particular application of the present invention, the product to be manufactured is used itself as the magnetic tape MS to be exposed to external physical and chemical agents. The "destructive" agent here is the manufacturing process itself which is put under control in response to sensed magnetic conditions, e.g., "alterations" set in the final product which determine the quality of the production output.

Figure 9:
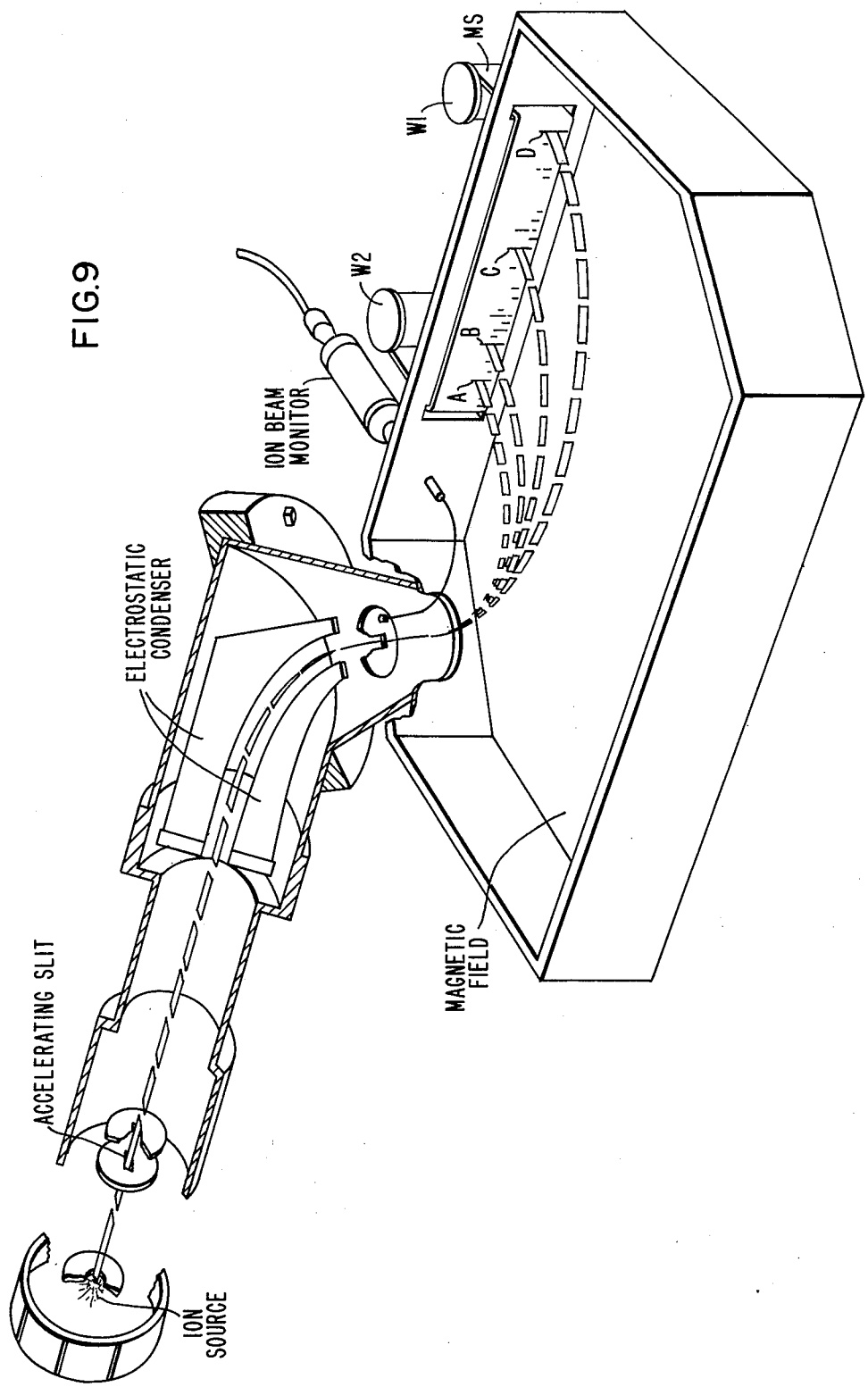
FIG. 9 is a diagrammatic representation of a mass spectrometer using the principles of the present invention.

FIG. 9 illustrates a novel and unique mass spectrometer making use of the inventive concept set forth in the present description. A mass spectrometer includes, as generally known, an ion source, the projected ions being expelled with various energies depending on the nature, e.g., the mass of the particular ion. A transverse magnetic field deflects the ions in motion to a different extent depending on their mass and individual velocity. Instead of the conventional plate which is exposed to chemical impact by such deflected ions, the present invention proposes to use a magnetic tape MS of the type described therein and it is such tape which, under the energy at the impact, is physically damaged to various degrees at several locations A, B, C, D. Thus, a spectrum of the chemical composition of the material used in the ion source is provided. This mass spectrometer offers definite advantages over mass spectrometers of the past. The tape MS may be moved continuously, or intermittently, when exposed, so that readings of the spectrum are obtained continuously as a function of time. Moreover, after impacting, the tape is permanently conditioned for ulterior reading by a magnetic sensor device. For this particular application, the structure of the tape MS preferably includes iron atoms imparting a strong magnetic quality to the tape. When metal is taken away under impact the magnetic characteristic are strongly modified.

The magnetic tape according to the invention may also consist of a metal such as copper, prepared by implantation of high energy iron ions into the base metal. Wherever the ion density is high, the magnetic quality of the tape is high, and conversely, where few or no iron ions have been implanted, the quality of the tape is low.

Such implantation of iron ions may be used in one application for the purpose of analyzing a phenomenon involving the emission of high energy ions. In another application it may be used to prepare the magnetic tapes according to the invention and make them capable of sensing external physical and chemical phenomena by self alteration, for instance by sputtering, leading to altered magnetic properties when exposed in accordance with the teachings set forth therein.

Another important application of the magnetic sensors according to the present invention relates to the metal processing industry. In this instance the vapor pressure from molten metal is used as a characteristic of the temperature of the bath. Since the vapor pressure is an exponential function of temperature, the alterations due to vapor particles impinging upon the surface of a magnetic tape will provide an excellent indication of temperature. From molten iron, for instance, will evolve iron particles of vapor to which a tape will be exposed continuously as a function of time. The tape may be unwound directly into a high temperature furnace such as used in the steel making industry.

With the same philosophy, it is conceivable to sense the condensation rate instead of the vaporization rate, as an expression of temperature, with tapes used according to the present invention in the same temperature detecting mode.

The preparation of magnetic tapes according to the present invention, as explained hereabove, must suit the requirements of the particular application, since a correlation must exist between the way the specific agent is attacking the material of the tape and the final magnetic property of the material to be sensed as a field or inductance variation.

The material may be glued as a layer on a substrate, electroplated, brazed, sintered, deposited. It may be in the form of a powder. It has been seen that it could be in the form of implanted ions. A very important factor in the preparation of the tapes according to the invention is the density of the magnetic domains since the resolution of information stored would depend strongly upon the density of the sensitive areas. While a low density increases the sensitivity considerably, it does not reduce the quality of the sensor since individual magnetic domains are capable of a very high density of information. For this reason, thin films of magnetic material are well suited for the purpose of the invention.

Density affects greatly the resolution obtained with the magnetic sensors according to the present invention, whenever an uneven physical or chemical impact by an outside agent is to be detected. The magnetic effect sensed with the electromagnetic bridge, such as the one disclosed in the aforementioned Hickam patent, can afford resolutions of the order of the micron on the surface of the tape. As a result, the magnetic tape according to the present invention permits the detection of the actual distribution of impinging or reacting particles. This is extremely important, for instance, for the chemical analysis of aerosols. This capability of the magnetic sensor is in this respect in line with what has been said hereabove with regard to its application as a mass spectrometer, or the use of vapor pressure as a characteristic of temperature.

I claim:

1. In a controlled industrial process, a method of monitoring at least one process condition variable consisting in the steps of:
    exposing as a function of time successive unwound regions of a reeled tape to structural alteration of said tape by said process condition variable, said structural alteration causing different magnetic properties in said tape;
    reeling said tape after exposure to said process condition variable;
    sensing electrically as a function of tape length a magnetic parameter of said tape as a representation of said structural alteration in said successive regions thereby deriving an electrical signal as a function of time; and
    correlating said electrical signal with said process condition variable;
    with the additional step of sampling material from said process, said tape being exposed to a predetermined chemical reaction with said sampled material, said chemical reaction causing said structural alteration of said tape.

2. The method of claim 1 with said process condition variable being temperature;
    with said tape being of material chemically altered in a predetermined high temperature range.

3. In a controlled industrial process, a method of monitoring at least one process condition variable consisting in the steps of:
    exposing as a function of time successive unwound regions of a reeled tape to structural alteration of said tape by said process condition variable;
    reeling said tape after exposure to said process condition variable, said structural alteration causing different magnetic properties in said tape;
    sensing electrically as a function of tape length a magnetic parameter of said tape as a representation of said structural alteration in said successive regions thereby deriving an electrical signal as a function of time; and
    correlating said electrical signal with said process condition variable;
    with said process condition variable being radiations generated by a nuclear reactor process;
    with said tape including material susceptible of physical swelling under exposure to said radiation, said structural alteration resulting from said physical swelling.

4. The method of claim 1 with said correlating step including the steps of:
    deriving a control signal from said derived electrical signal; and
    controlling said process variable in response to said control signal.

5. In a controlled industrial process, a method of monitoring at least one process condition variable consisting in the steps of:

exposing as a function of time successive unwound regions of a reeled tape to structural alteration of said tape by said process condition variable, said structural alteration causing different magnetic properties in said tape;

reeling said tape after exposure to said process condition variable;

sensing electrically as a function of tape length a magnetic parameter of said tape as a representation of said structural alteration in said successive regions thereby deriving an electrical signal as a function of time; and correlating said electrical signal with said process condition variable;

with said process condition variable being the vapor evolving from a high temperature body, with said tape being exposed to said vapor in proximity to said body whereby the physical nature of said tape is altered by said particle in said vapor, and said electrical signal is indicative of the temperature of said body.

6. In a controlled industrial process, a method of monitoring at least one process condition variable consisting in the steps of:

exposing as a function of time successive unwound regions of a reeled tape to structural alteration of said tape by said process condition variable;

reeling said tape after exposure to said process condition variable;

sensing electrically as a function of tape length a magnetic parameter of said tape as a representation of said structural alteration in said successive regions thereby deriving an electrical signal as a function of time; and correlating said electrical signal with said process condition variable;

which said process condition variable being the condensate evolving from a high temperature vapor with said tape being exposed to said condensate, whereby the physical nature of said tape is altered by said condensate and said electrical signal is indicative of the temperature of said vapor.

7. A tape for the on-line recording of a process condition variable comprising:

an inorganic material having a selected composition which is susceptible of acquiring different magnetic properties as a result of exposure to said process condition variable, the resulting magnetic properties of said material being in a predetermined relation to the exposure to said process condition variable, and said material having a chemical composition susceptible of reacting chemically when exposed to said process condition variable, different magnetic properties of said material being established at successive locations along said tape in predetermined relation to exposure and the resulting chemical reaction; whereby a recording as a function of time of said process condition variable is obtained along the exposed tape.

8. The tape of claim 7 with said process condition variable including a chemical agent susceptible of reacting with said chemical composition to form a chemical compound, said chemical compound being formed to variable amounts on said magnetic tape, thereby to affect the magnetic properties of said tape in relation to said amounts.

9. The tape of claim 8 with said variable amounts being formed in variable amounts spatially distributed on said tape, thereby to create localized changes in the magnetic properties of said tape.

10. The tape of claim 8 with said agent including sulfur as a chemical element, and said compound being a sulfur containing compound.

11. The tape of claim 8 with said agent including hydrogen as a chemical element, and said compound being a hydrogen containing compound.

12. The tape of claim 8 with said agent including nitrogen as a chemical element, and said compound being a nitrogen containing compound.

13. The tape of claim 8 with said agent including carbon as a chemical element, and said compound being a carbon containing compound.

14. The tape of claim 8 with said agent including a halogen as a chemical element, and said compound being a halogen containing compound.

15. The tape of claim 8 with said agent including oxygen as a chemical element, and said compound being an oxygen containing compound.

16. The tape of claim 8 with said agent being water, with said material being metallic and said compound being a metallic oxide.

17. In a controlled industrial process, the method of monitoring at least one process condition variable existing at a high temperature, consisting in the steps of:

exposing at said high temperature as a function of time successive unwound regions of a reeled tape of inorganic material susceptible of undergoing a chemical reaction to form an inorganic reaction product thereon under said process condition variable;

reeling said tape after exposure to said process condition variable at said high temperature;

said high temperature being above the Curie temperatures of at least one of said tape material and reaction product; whereby at least one of said tape and said reaction product is non-magnetic when exposed to said high temperature;

sensing electrically with said tape below said Curie temperatures as a function of time a magnetic parameter of at least one of said tape material and chemical product as a representation of the intensity of said tape material and chemical product as a representation of the intensity of said chemical reaction in said successive regions, thereby deriving an electrical signal as a function of time; and correlating said electrical signal with said process condition variable.

18. A method of recording as a function of time the magnitude of a process variable involving an industrial process and a chemical agent generated thereby in amount related to said process variable magnitude, comprising:

selecting a tape of material having an inorganic constituent susceptible of forming reacted material by chemical reaction with said agent, the reacted material having magnetic properties different from said constituent;

exposing successive portions of said tape to said industrial process to cause the formation of variable amounts of reacted material thereon; and retrieving successively the exposed portions of said tape from said industrial process.

19. The method of claim 18 further including the step of detecting changes in the magnetic properties of said tape as a result of said step of exposing the tape, and of deriving a signal characteristic of said changes as a function of time to provide a representation of variations in the magnitude of said process variable.

20. The method of claim 18, with said tape consisting of a core wire coated with said inorganic constituent.

21. The method of claim 18, with said tape comprising a substrate having a thin film of said inorganic constituent thereon.

22. The method of claim 18 with said tape comprising a substrate, said inorganic constituent being in powder form and deposited thereon.

23. The method of claim 18, with said tape comprising a substrate, said inorganic constituent being sintered thereon.

24. The method of claim 18 with said tape comprising a substrate, said inorganic constituent being implanted on said substrate by high energy ions of said inorganic constituent.

25. The method of claim 18 with said tape comprising an inorganic substrate, said inorganic constituent being obtained by chemical reaction effected on said substrate.

26. The method of claim 18, with said inorganic constituent being an oxide, the exposure being by chemical reduction.

27. The method of claim 18, with said inorganic constituent being susceptible of chemical oxidation when exposed to said process condition variable, and said chemical agent being oxygen.

* * * * *